(12) United States Patent
Richardson et al.

(10) Patent No.: US 9,053,290 B2
(45) Date of Patent: *Jun. 9, 2015

(54) METHOD AND SYSTEM OF ESTIMATING THE CROSS-SECTIONAL AREA OF A MOLECULE FOR USE IN THE PREDICTION OF ION MOBILITY

(75) Inventors: Keith George Richardson, Derbyshire (GB); Iain David Grant Campuzano, Westlake Village, CA (US)

(73) Assignee: Micromass UK Limited, Wilmslow (GB)

( * ) Notice: Subject to any disclaimer, the term of this patent is extended or adjusted under 35 U.S.C. 154(b) by 803 days.
This patent is subject to a terminal disclaimer.

(21) Appl. No.: 13/264,039

(22) PCT Filed: Apr. 15, 2010

(86) PCT No.: PCT/GB2010/050625
§ 371 (c)(1),
(2), (4) Date: Jan. 23, 2012

(87) PCT Pub. No.: WO2010/119289
PCT Pub. Date: Oct. 21, 2010

(65) Prior Publication Data
US 2012/0116690 A1 May 10, 2012

Related U.S. Application Data

(60) Provisional application No. 61/185,322, filed on Jun. 9, 2009.

(30) Foreign Application Priority Data

Apr. 15, 2009 (GB) .................................. 0906466.8
Apr. 15, 2009 (GB) .................................. 0906467.6

(51) Int. Cl.
*G06F 19/00* (2011.01)
*G06G 7/58* (2006.01)
*G01N 27/62* (2006.01)
*G06F 19/16* (2011.01)

(52) U.S. Cl.
CPC ............ *G06F 19/701* (2013.01); *G01N 27/622* (2013.01); *G06F 19/16* (2013.01); *G06F 19/704* (2013.01)

(58) Field of Classification Search
CPC ..... G01N 27/622; G06F 19/16; G06F 19/701; G06F 19/704
USPC ............... 702/12, 19, 28, 150, 156; 703/1, 11
See application file for complete search history.

(56) References Cited

U.S. PATENT DOCUMENTS

| | | | | |
|---|---|---|---|---|
| 8,280,699 B2 * | 10/2012 | Ichishima et al. | ................ | 703/1 |
| 8,655,600 B2 * | 2/2014 | Richardson et al. | ............ | 702/19 |

FOREIGN PATENT DOCUMENTS

| | | |
|---|---|---|
| JP | 2001/503195 | 3/2001 |
| JP | 2012/524316 | 10/2012 |

(Continued)

OTHER PUBLICATIONS

Jin et al; "Conformation of glycosaminoglycans by ion mobility mass spectrometry and molecular modelling"; Phys. Chem. Chem. Phys. 2005, 7, pp. 3464-3471, XP-002592102, ISSN: 1463-9076.

(Continued)

*Primary Examiner* — John H Le
(74) *Attorney, Agent, or Firm* — Diederiks & Whitelaw, PLC

(57) ABSTRACT

A method of estimating the cross-sectional area of a molecule for use in the prediction of ion mobility gives gas phase interaction radii determination and cross-sectional algorithm computation to provide separation and characterization of structurally related isomers. More specifically, the invention provides a method of correlating the differences in the molecular structures with differences in anti-cancer activity of pre-determined anti-cancer drugs by utilizing a new algorithm for estimating the cross-sectional area of the molecules of such drugs.

14 Claims, 1 Drawing Sheet

(56) References Cited

FOREIGN PATENT DOCUMENTS

WO  2010/119289  10/2010
WO  2010/119293  10/2010

OTHER PUBLICATIONS

Mack Jr., Edward; "Average cross-sectional areas of molecules by gaseous diffusion methods" Journ of Am. Chem. Soc. USA, vol. 47, Oct. 1925, pp. 2468-2482, SP002592103.

Mosier, et al; "Prediction of peptide ion collision cross sections from topological molecular structure and amino acid parameters" Anal. Chem. vol. 74, No. 6, Mar. 15, 2002, pp. 1360-1370, XP002592104.

PCT International Written Opinion for application No. PCT/GB2010/050625, dated Oct. 20, 2010, Form PCT/ISA/237.

PCT International Search Report for application No. PCT/GB2010/050625, dated Oct. 20, 2010, Form PCT/ISA/210.

http://www.indiana.edu/~nano/Software.html Jan. 20, 2015.

* cited by examiner

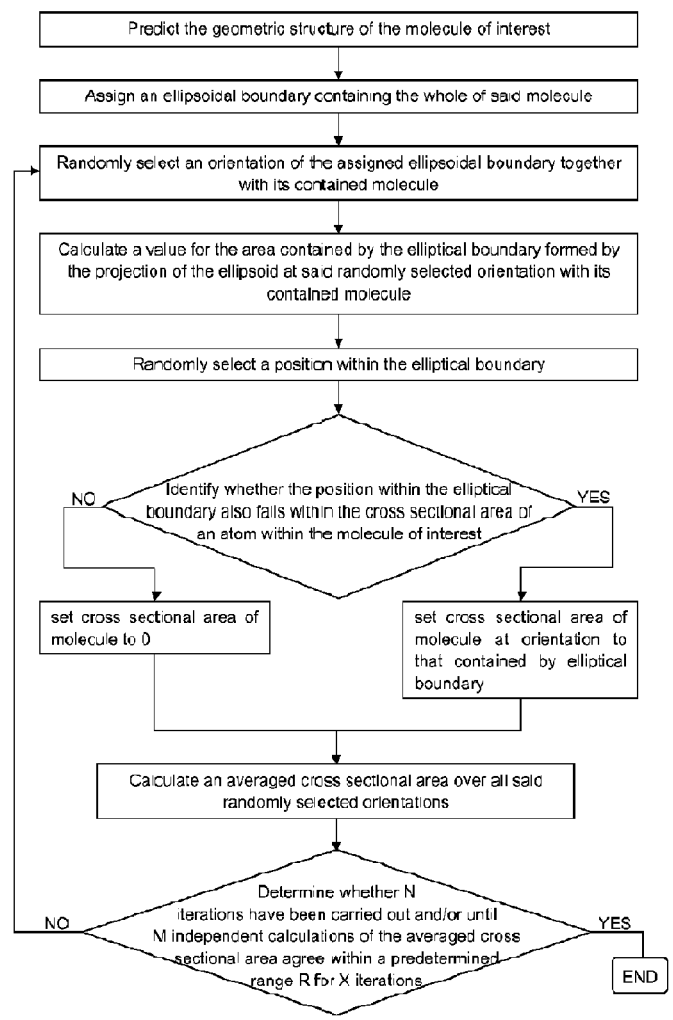

METHOD AND SYSTEM OF ESTIMATING THE CROSS-SECTIONAL AREA OF A MOLECULE FOR USE IN THE PREDICTION OF ION MOBILITY

This invention relates to a method of estimating the cross-sectional area of a molecule for use in the prediction of ion mobility for a wide range of molecular species.

Ion mobility has the potential to separate isomeric species based on differences in gas phase collision cross-sections ($\Omega$) and can provide valuable information on ionic conformation through comparisons with theoretical models. However, to relate the ion mobility derived collision cross-section of a molecule to its structure accurately, it is necessary to obtain prior knowledge of the gas phase radii of the constituent atoms.

The molecular cross-section is approximated as the rotationally averaged area of the "shadow" cast by the molecule. The term "shadow" is used to refer to the projection of a molecule, atom or ellipsoid onto any plane. The plane employed remains fixed throughout the calculation.

The projection approximation (PA) has been shown to be a useful method of calculating the cross-section of a molecule to be used in the prediction of ion mobility. It is not possible to calculate the projection approximation cross-section directly, but it is possible to obtain numerical approximations using Monte Carlo techniques. Monte Carlo methods are a class of computational algorithms that rely on repeated random sampling to compute their results and often are used when it is infeasible or impossible to compute an exact result with a deterministic algorithm.

It is known to obtain prior knowledge of the gas phase radii of the constituent atoms of a molecule by means of an algorithm known as MobCal (http://www.indiana.edu/~nano/Software.html) which includes the following steps:—

(1) Set A=O, n=O, and
(2) select a random orientation of the molecule
(3) select a rectangle bounding the molecular shadow and calculate the area of the rectangle=area Abox,
(4) select a point randomly within the rectangle,
(5) if the point lies within the molecular shadow, then A=A+Abox
(6) n=n+1
(7) if n<$n_{max}$ GOTO 2
   (i.e. select another random orientation of the molecule for the next iteration)
(8) End. Result is A/n However, there are at least two potential (but related) problems with this approach. First, in the selection of $n_{max}$, it is difficult if not impossible to know how many orientations (step 2) are sufficient, and secondly there are situations in which convergence is slow so that naive convergence tests can be misleading.

The above algorithm can be improved to allow more than one selection per orientation giving a modified algorithm.

One aspect or feature of the invention provides a method of estimating the cross sectional area of a molecule, e.g. for determining the characteristics of predetermined or sample molecules, the method the steps of:
(1) Set A=O, n=O, and
(2) select a random orientation of the molecule
(3) select a rectangle bounding the molecular shadow and calculate the area of the rectangle=area Abox
(4) select K points randomly within the rectangle
(5) for each point that lies in the molecular shadow, A=A+Abox/K
(6) n=n+1
(7) if n<$n_{max}$ GOTO 2 (next iteration)
(8) End. Result is A/n The above method will be referred to hereinafter as the 'rectangle' method.

However, the present invention involves a further improvement of the previously known Mobcal algorithm to produce a more efficient implementation of the Mobcal type calculation to provide improved confidence in convergence of the rotationally averaged cross section, obtained to a user-specified accuracy.

Another aspect of the present invention provides a method of estimating the cross sectional area of a molecule, e.g. for determining the characteristics of predetermined or sample molecules, the method comprising the steps of:—

A) Predicting the geometric structure of the molecule of interest;
B) Assign an ellipsoidal boundary containing the whole of said molecule;
C) Randomly selecting an orientation of the assigned ellipsoidal boundary together with its contained molecule;
D) Calculate a value for the area contained by the elliptical boundary formed by the projection of the ellipsoid at said randomly selected orientation;
E) Randomly selecting a position within the elliptical boundary;
F) Identify whether the position within the elliptical boundary also falls within the cross sectional area of an atom within the molecule of interest;
G) If said F) criterion is met, set said cross sectional area of the molecule at said orientation to the cross sectional area contained by the elliptical boundary calculated in D, if said F criteria is not met, set said cross sectional area of the molecule to 0;
H) Calculate an averaged cross sectional area over all said randomly selected orientations;
I) iterate steps C) to H) for at least N iterations and/or until M independent calculations of the averaged cross sectional area agree within a predetermined range R for X iterations.

The above method will be referred to hereinafter as the 'ellipsoidal rejection sampling' method.

According to a feature of the invention the value of N may be between 0 and 50, for example between 0 and 30 or between 20 and 50 or between 10 and 40.

According to another feature of the invention the value of M may be between 1 and 20, for example between 1 and 10 or 1 and 5 or alternatively between 10 and 20 or 15 and 20 or alternatively between 5 and 15.

According to another feature of the invention the value of R may be between 0.1 and 20%, for example 1 and 20% or alternatively between 0.1 and 1%.

[Note that R can be a percentage or an absolute value]

According to another feature of the invention the value of X may be between 1 and 20, for example between 1 and 10 or 1 and 5 or alternatively between 10 and 20 or 15 and 20 or alternatively between 5 and 15.

Another aspect of the invention provides a method of determining characteristics of predetermined molecules (e.g. small molecules and proteins, peptides, oligoneucleotides and glycans) comprising the use of a combined ion mobility—mass spectrometry (IM-MS) technique for experimentally determining a range of molecular structures and comparing values that range with those derived by an estimating method according to any of the three immediately preceding paragraphs so as to correlate the differences in the molecule structures with differences in selected predetermined activity of those molecules.

According to a feature of this aspect of the invention, the method may correlate the differences in the molecular structures with differences in anti-cancer activity of predetermined anti-cancer drugs. Preferably, the anti cancer drugs are organometallic based drugs. Preferably, the organometallic drugs are isomeric Ru-based.

According to another feature of this aspect of the invention, the IM-MS technique may include the use of travelling wave (T-wave) mobility separation.

The method of the present invention gives gas phase interaction radii determination and cross-section algorithm computation to provide separation and characterisation of structurally related isomers by ion mobility.

A further aspect of the invention provides a system for determining characteristics of predetermined molecules, the system comprising an ion mobility cell, a mass spectrometer and a processor programmed or configured to determine experimentally a range of molecular structures and compare values of that range with those derived by an estimating method described above so as to correlate the differences in the molecular structures with differences in selected predetermined activity of those molecules.

A yet further aspect of the invention provides a computer program element comprising computer readable program code means for causing a processor to execute a procedure to implement the method described above.

The computer program element may be embodied on a computer readable medium.

A yet further aspect of the invention provides a computer readable medium having a program stored thereon, where the program is to make a computer execute a procedure to implement the method as described above.

An embodiment of the invention will now be described, by way of example only, with reference to the accompanying drawing, wherein:

FIG. 1 is a flow chart illustrating an algorithm according to an embodiment of the present invention.

One algorithm of the present invention is as follows:—
A) Predicting the geometric structure of the molecule of interest;
B) Assign an ellipsoidal boundary containing the whole of said molecule;
C) Randomly selecting an orientation of the assigned ellipsoidal boundary together with its contained molecule;
D) Calculate a value for the area contained by the elliptical boundary formed by the projection of the ellipsoid at said randomly selected orientation;
E) Randomly selecting a position within the elliptical boundary;
F) Identify whether the position within the elliptical boundary also falls within the cross sectional area of an atom within the molecule of interest;
G) If said F) criterion is met, set said cross sectional area of the molecule at said orientation to the cross sectional area contained by the elliptical boundary calculated in D, if said F criteria is not met, set said cross sectional area of the molecule to 0;
H) Calculate an averaged cross sectional area over all said randomly selected orientations;
I) Iterate steps D) to H) for at least N iterations and/or until M independent calculations of the averaged cross sectional area agree within a predetermined range R for X iterations For many molecules, this ellipsoidal rejection sampling algorithm will converge to the desired result faster than that of the prior art algorithms referred to.

The following termination procedure has been implemented in conjunction with the above algorithm:—
(1) Instantiate N projection approximation calculations (henceforth called objects);
(2) perform iterations for each of these objects in turn, keeping running area estimates for each object;
(3) terminate when the area estimates for all objects agree with a user specified tolerance (either percentage or absolute), reporting the overall average of these estimates as the result.

The IMS device of a mass spectrometer was calibrated using a haemoglobin peptide mixture and other compounds of known collisional cross section, such as polyglycine (http://www.indiana.edu/~clemmer/Research/research.htm); a calibration coefficient was then derived. The ion mobility of each small molecule was measured and therefore the experimental collision cross section (CCS) determined. The radius of each of the atoms, specific to an individual small molecule were then "tuned" within the CCS algorithm such that the output of the CCS algorithm closely matched the experimentally derived CCS values for each of the small molecules analysed. An optimal interaction radius value ($Å^2$) for C, H, O, S, Cl, F, N & Ru were thus derived.

The small molecules used to optimise the CCS algorithm were: C60, C70, pyrene, camphene, phenanthrene, triphenylene, naphthalene, ampicillin, spermine, lorazepam, caffeine, reserpine, raffinose, nifedipine, nimodipine, dexamethazone, diphenylhydramine, metoprolol, glutathione, cysteine, apomorphine, erythromycin, oxytetracyclin, verapamil, salbutamol, acetylsalicylic acid, the 20 naturally occurring common amino acids, angiotensin II, oxytocin, testosterone, ibuprofen, beta-cyclodextrin and the ruthenium containing compounds ru-ortho (and associated HCl neutral loss species), ru-meta (and associated HCl neutral loss species), ru-para (and associated HCl neutral loss species).

Certain organometallic drugs are used in the fight against cancer. The platinum-based drug, cisplatin [cis-diamminedichloridoplatinum(II)], for example, falls into this category and is one of the leading drugs used in the fight against cancer. DNA is a potential target for many metal-based anticancer drugs and distortions of DNA structure often correlate with anticancer activity. Other metal-based anticancer drugs, such as those based on ruthenium, are being developed as alternative treatments to combat cancer. In particular, the aim is to widen the spectrum of anticancer activity, reduce unwanted side effects, and avoid cross-resistance with cisplatin and related drugs. Insights into the physical size and shape of these novel Ru-based drugs are important for elucidation of structure-activity relationships and for optimizing key interactions such as intercalation into DNA. Three novel isomeric Ru-based anticancer drugs have been explained using a combined ion mobility and mass spectrometry (IM-MS) approach together with an estimating method according to the invention.

As a stand-alone technique, MS cannot separate isomeric species or provide bulk structural conformational information. However, IM has the ability to rapidly separate isomeric species (on the MS acquisition timescale) based on differences in their collision cross sections (CCS; physical size and shape) in the gas phase, thus providing specific information on ionic configuration. The combination of IM with MS provides an extremely powerful analytical tool.

To investigate the possible benefits of the IM-MS technique, an instrument that is based around "traveling-wave" (T-wave) mobility separation was used to analyze a mixture of three low-molecular-weight isomeric ruthenium terphenyl anticancer complexes (m/z 427.1 based on [102]Ru). Individual differences in shape have been studied in an attempt to correlate them with differences in anticancer activity. Molecular modelling was also used to generate a range of possible structures and the theoretical CCSs for these structures were calculated for comparison with experimentally derived T-wave values. Excellent agreement was observed between the experimentally and theoretically derived CCS measurements.

The ion mobility derived gas phase interaction radii in combination with the new CCS algorithm, molecular modelling and ion mobility mass spectrometry for the separation and conformational analysis of three low-molecular-weight isomeric organoruthenium anti-cancer complexes containing ortho-, meta- or para-terphenyl arene ligands (Mw 427.1) and the subsequent isomeric HCl neutral loss species (Mw 391.1) has been used in accordance with the invention. The six isomeric compounds showed well defined arrival time distributions allowing experimental collision cross-sections to be calculated and compared to theoretical values. Excellent agreement was observed between all experimentally- and theoretically-derived results. The difference in shape of the elongated terphenyl arene compared to the more compact shapes is likely to make an important contribution to the significantly higher anti-cancer activity of the elongated structure.

In summary, the invention reports inferred gas phase interaction radii for H, C, and the previously uninvestigated O, S, Cl, F, N, Fe, Pt and Ru. Furthermore, the method of the present invention demonstrates for the first time that isomeric ruthenium (II) terphenyl anticancer complexes, whose CCSs differ by less than $9.0 \text{ Å}^2$, can be separated and characterised by travelling wave ion mobility.

As an extreme example consider the C60 or "Buckminsterfullerene" molecule which consists of 60 carbon atoms arranged on the surface of a hollow sphere of radius R. Projections of this molecule are roughly circular.

Using a rectangular boundary for each trial orientation, and performing the rotations around the centre of the molecule, the acceptance rate is roughly the area of a circle of radius R divided by the area of a square of radius 2R which is $(\pi R^2)/(4R^2)=\pi/4$ or 0.785.

A suitable ellipsiodal boundary is a sphere of radius R, and the projections of this are always a circle of radius R. In this case acceptance rate is roughly 0.97.

In a series of 10 trials with ten shots per orientation, the ellipsoidal method converged to the required precision with, on average, five times fewer iterations than the rectangular method.

The table below shows results that were obtained using the Mobcal algorithm as compared with the rectangle and ellipsoidal rejection sampling methods.

| Compound | Mobcal | Rectangle | Ellipsoidal Rejection Sampling |
| --- | --- | --- | --- |
| C60 | 1 minute | 0.064 seconds | 0.015 seconds |
| 1IHM_FULL | 26 hours | 121 seconds | 36 seconds |

It will be appreciated by those skilled in the art that any number of combinations of the aforementioned features and/or those shown in the appended drawing provide clear advantages over the prior art and are therefore within the scope of the invention described herein.

The invention claimed is:

1. A method of estimating a cross sectional area of a molecule of interest with a processor comprising the steps of:
    A) Developing, by the processor, a predicted geometric structure of the molecule of interest;
    B) Assigning, by the processor, an ellipsoidal boundary containing all of said molecule of interest;
    C) Randomly selecting, by the processor, an orientation of the assigned ellipsoidal boundary together with the molecule of interest;
    D) Calculating, by the processor, a value for an area contained by an elliptical boundary formed by a projection of the ellipsoid at said randomly selected orientation;
    E) Randomly selecting, by the processor, a position within the elliptical boundary;
    F) Identifying, by the processor, whether the position within the elliptical boundary also falls within the cross sectional area of an atom within the molecule of interest;
    G) If said position within the elliptical boundary also falls within the cross sectional area of any atom within the molecule of interest then setting, by the processor, said cross sectional area of the molecule at said orientation to the cross sectional area contained by the elliptical boundary calculated in step D, if said position within the elliptical boundary does not fall within the cross sectional area of the atom within the molecule of interest then setting, by the processor, said cross sectional area of the molecule to 0;
    H) Calculating, by the processor, an averaged cross sectional area over all said randomly selected orientations wherein at least steps G) and H) are preformed with the processor;
    I) Iterating, by the processor, steps D) to H) for at least N iterations or until M independent calculations of the averaged cross sectional area agree within a predetermined range R for X iterations.

2. A method according to claim 1, wherein the value of N is between 1-50.

3. A method according to claim 1, wherein the value of M is between 1-20.

4. A method according to claim 1, wherein the value of R is between 1 and 20%.

5. A method according to claim 1, wherein the value of X is between 1 and 20.

6. A method according to claim 1 further comprising determining characteristics of predetermined molecules comprising the use of a combined ion mobility-mass spectrometry (IM-MS) technique for experimentally determining a range of molecular structures and
    comparing the characteristics determined with the mass spectrometry technique with those derived by the estimating the cross sectional area of a molecule of interest so as to correlate the differences in the molecular structures with differences in selected predetermined activity of those molecules.

7. A method according to claim 6 wherein the method correlates the differences in the molecular structures with differences in anti-cancer activity of predetermined anti-cancer drugs.

8. A method according to claim 7 wherein the anti-cancer drugs are organometallic based drugs.

9. A method according to claim 8 wherein the organometallic drugs are isomeric Ru-based.

10. A method according to claim 7, wherein the IM-MS technique includes the use of travelling wave (T-wave) mobility separation.

11. A computer program element comprising computer readable program code means for causing a processor to execute a procedure to implement the method of claim 1.

12. Computer program element according to claim 11 embodied on a computer readable medium.

13. A computer readable medium having a program stored thereon, where the program is to make a computer execute a procedure to implement the method of claim 1.

14. A system for determining characteristics of predetermined molecules, the system comprising an ion mobility cell, a mass spectrometer and a processor programmed or configured to determine experimentally a range of molecular structures and compare values of that range with those derived by a method of estimating a cross sectional area of a molecule of interest, said the system further comprising a non-transitory computer readable medium having a computer program executed by said processor to perform the steps of:
  A) Developing a predicted geometric structure of the molecule of interest;
  B) Assigning an ellipsoidal boundary containing all of said molecule of interest;
  C) Randomly selecting an orientation of the assigned ellipsoidal boundary together with the molecule of interest;
  D) Calculating a value for an area contained by an elliptical boundary formed by a projection of the ellipsoid at said randomly selected orientation;
  E) Randomly selecting a position within the elliptical boundary;
  F) Identifying whether the position within the elliptical boundary also falls within the cross sectional area of an atom within the molecule of interest;
  G) If said position within the elliptical boundary also falls within the cross sectional area of any atom within the molecule of interest then setting said cross sectional area of the molecule at said orientation to the cross sectional area contained by the elliptical boundary calculated in step D, if said position within the elliptical boundary does not fall within the cross sectional area of the atom within the molecule of interest then setting said cross sectional area of the molecule to 0;
  H) Calculating an averaged cross sectional area over all said randomly selected orientations wherein at least steps G) and H) are preformed with the processor in the system;
  I) Iterating steps D) to H) for at least N iterations or until M independent calculations of the averaged cross sectional area agree within a predetermined range R for X iterations so as to correlate the differences in the molecular structures with differences in selected predetermined activity of those molecules.

* * * * *